United States Patent
Rank et al.

(10) Patent No.: US 11,135,478 B1
(45) Date of Patent: Oct. 5, 2021

(54) VIRTUAL POWER ATHLETIC PERFORMANCE METRIC

(71) Applicant: Inspyridon Technologies, LLC, Burlingame, CA (US)

(72) Inventors: Jeffrey Rank, San Mateo, CA (US); Douglas Woods, Burlingame, CA (US)

(73) Assignee: Inspyridon Technologies, LLC, Burlingame, CA (US)

( * ) Notice: Subject to any disclaimer, the term of this patent is extended or adjusted under 35 U.S.C. 154(b) by 485 days.

(21) Appl. No.: 15/885,280

(22) Filed: Jan. 31, 2018

Related U.S. Application Data

(60) Provisional application No. 62/452,586, filed on Jan. 31, 2017.

(51) Int. Cl.
*A63B 24/00* (2006.01)

(52) U.S. Cl.
CPC .. *A63B 24/0062* (2013.01); *A63B 2024/0065* (2013.01)

(58) Field of Classification Search
CPC ................ A63B 69/32; A63B 24/0062; A63B 2024/0065
See application file for complete search history.

(56) References Cited

U.S. PATENT DOCUMENTS

| | | | | |
|---|---|---|---|---|
| 6,013,007 | A * | 1/2000 | Root | A63B 24/0006 482/8 |
| 8,768,648 | B2 | 7/2014 | Panther et al. | |
| 8,954,289 | B2 | 2/2015 | Burton et al. | |
| 2003/0216228 | A1 * | 11/2003 | Rast | A63B 47/021 482/84 |
| 2011/0118086 | A1 * | 5/2011 | Radow | A63B 24/0062 482/5 |

FOREIGN PATENT DOCUMENTS

WO 2016044831 A1 3/2016

OTHER PUBLICATIONS https://www.trainingpeaks.com/blog/running-with-power-how-it-works-and-what-it-means/; Dec. 5, 2016; retrieved from website on Dec. 7, 2018.
https://www.youtube.com/watch?v=pqACzgjVxqs; Andrew Coggan; Apr. 20, 2016; Apr. 20, 2016; retrieved from website on Dec. 7, 2018.
https://www.outsideonline.com/1981811/science-behind-stryd-worlds-first-running-power-meter; May 27, 2015; retrieved from website on Dec. 7, 2018.
https://www.dcrainmaker.com/2015/01/stryd-first-running.html; Jan. 30, 2015; retrieved from website on Dec. 7, 2018.
https://www.dcrainmaker.com/2016/08/stryd-running-power-meter-v2.html; Aug. 24, 2016; retrieved from website on Dec. 7, 2018.
https://www.trainingpeaks.com/blog/how-running-power-meters-work/; Aug. 30, 2016; retrieved from website on Dec. 7, 2018.
https://www.kickstarter.com/projects/scribeformakers/runscribe-wearable-for-the-data-driven-athlete; Aug. 20, 2014; retrieved from website on Dec. 7, 2018.
https://www.slowtwitch.com/Products/RPM2_Measurement_Insoles_3825.html; Aug. 17, 2013; retrieved from website on Dec. 7, 2018.

\* cited by examiner

*Primary Examiner* — Elias Desta
(74) *Attorney, Agent, or Firm* — Avyno Law P.C.

(57) ABSTRACT

The invention is a system and method for measuring real-time athletic performance. It provides runners or other endurance athletes with a real-time training metric. Rather than attempt to measure the athlete's real-time power output, which is a complicated measurement unproven outside the laboratory, an athlete's performance and environmental conditions (speed, acceleration, incline, running surface, and wind) are measured and used to predict virtual power in real-time.

21 Claims, 7 Drawing Sheets

VIRTUAL POWER ATHLETIC PERFORMANCE METRIC

CROSS-REFERENCE TO RELATED APPLICATIONS

This application claims priority to U.S. Provisional application 62/452,586, titled System and Methods for measuring athletic performance, by Jeffrey Rank and Douglas Woods, filed on Jan. 31, 2017, which is incorporated by reference herein.

FIELD OF INVENTION

The invention relates to measuring real-time athletic performance and, in particular, an athlete's virtual power in real time.

BACKGROUND

Jack Daniels, A running coach in the 1970's examined the performance and known $VO_2MAX$ values of elite middle and long distance runners. Although $VO_2MAX$ values varied between equally performing runners, he assigned equally performing runners equal aerobic profiles, called "pseudo$VO_2MAX$" or VDOT values for short. VDOT values determined in this way were based on performance and encompassed many factors that determine a runner's ability including $VO_2MAX$, running economy, biomechanics, and mental toughness. Because VDOT provided a holistic view of a runner's ability, Daniel's concludes that VDOT is a better measure to assess fitness and determine training paces. Furthermore, Daniels used VDOT calculated from the results of a recent competition to determine equivalent performances across different race distances.

The current invention builds on the concept of VDOT by extending it from a single measure summarizing an athlete's race performance to a real-time metric that can provide continuous feedback to an athlete while training/competing. The concept is further extended to account for additional factors that can impact an athlete's pacing and performance, such as incline, wind resistance, and acceleration, thus allowing an athlete to adjust pacing and analyze performance across a wide range of conditions.

Other known approaches claim to measure real-time running power and/or running economy directly. But, the problem with the prior art is that accurately measuring an athlete's or, more particularly, a runner's, real power output and running efficiency is very difficult using a simple clip on device. The problem exists because a significant portion of the energy of the runner is stored elastically in muscles and tendons during the impact phase of each stride. This stored energy is subsequently released to propel the runner forward and into the air. Even if the ground reaction forces of the runner are measured precisely, it is not possible to tell the difference between forces generated by the release of elastically stored energy, and forces generated by contracting muscles generating real power output.

Thus, direct measurement of changes in a runner's economy as he or she transitions up and down hills is unproven outside of the laboratory where running economy can be determined through directly measuring an individual's rate of oxygen consumption.

SUMMARY

Rather than attempt to measure a runner's real power output, which must include a measure of running economy, running conditions are measured to accurately predict a runner's virtual power in real-time. Published laboratory data is used on the running economy of excellent runners under a variety of running conditions to predict virtual power based solely on running conditions. Virtual power is analogous to VDOT in that it provides a holistic measure of running performance that encompasses many factors including V02MAX, running economy, biomechanics, and mental toughness. However, unlike VDOT, virtual power can be measured in near real-time and will vary not just with pace, but also with slope, wind, acceleration, and running surface. Therefore, virtual power is not a measure of a runner's actual power output but rather a measure of the equivalent power it would take for an excellent runner to run under the conditions that a runner is currently running under. Virtual power cannot be used to calculate a runner's running economy and in fact assumes the running economy of an excellent runner. This approach enables reliable real-time calculation of the power requirement for a runner under current conditions (speed, acceleration, incline, running surface and wind) and provides a quick and reliable performance metric.

Virtual power is a real-time measure of running performance that combines a runner's actual power output and running economy into a single power performance metric. A runner's virtual power is determined by calculating the ideal power produced by an excellent runner of similar weight running under current running conditions (incline, speed, acceleration, running surface, and wind). Since virtual power is calculated from current running conditions, all runners of equal weight under the same conditions will generate the same virtual power. This is despite individual differences in running economy which may make the real power output higher or lower by a few percent. This solution allows runners to compare virtual power from runner to runner as power/weight. Moreover, virtual power assumes no changes in running economy during a run so virtual power estimates will be the same even as fatigue sets in and an individual loses running economy.

BRIEF DESCRIPTION OF THE FIGURES

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Figure 1:
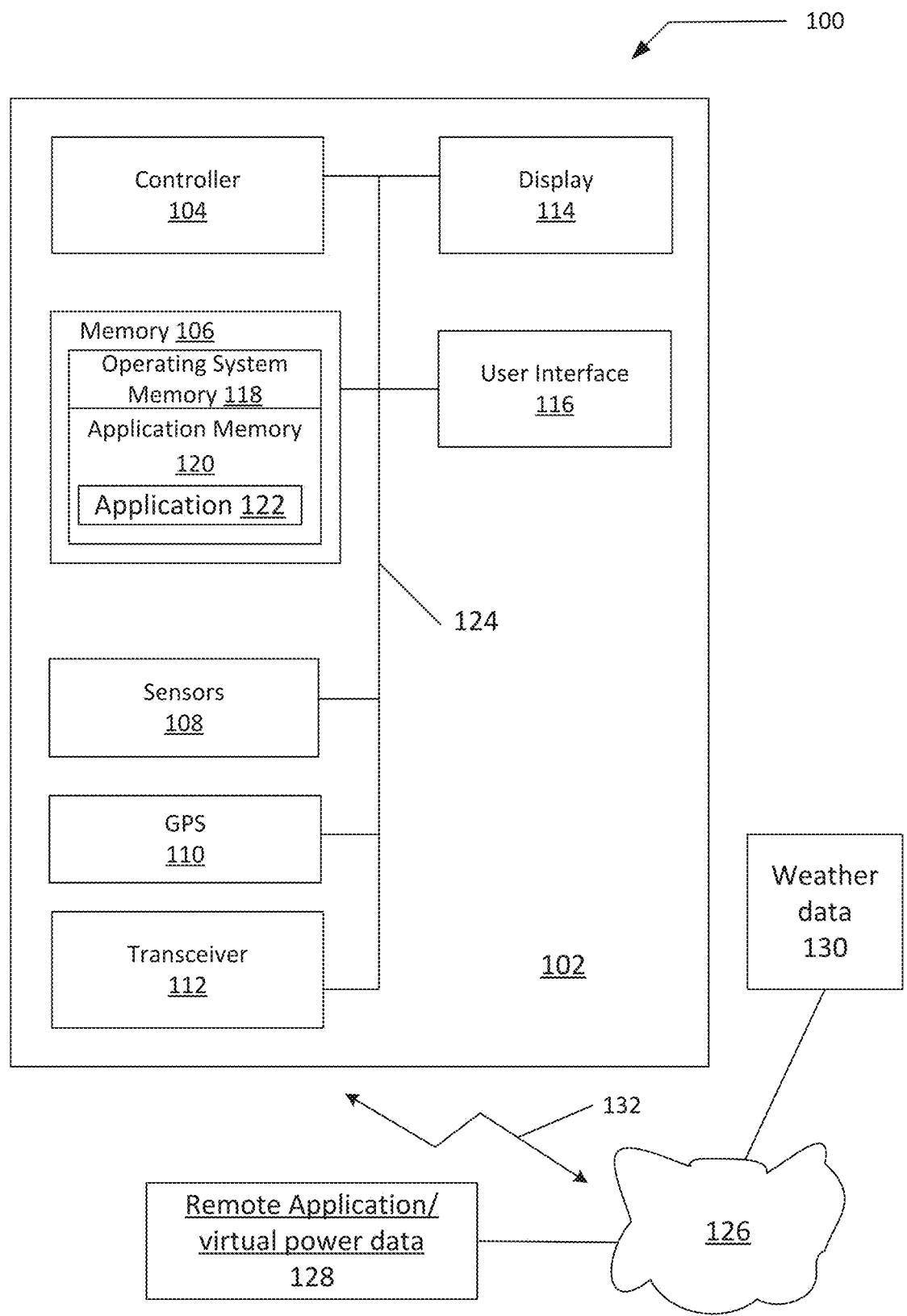
FIG. 1 shows a block diagram of a smart device in accordance with an example of an implementation of the invention.

Virtual power is a real-time measure of running performance that combines a runner's actual power output and running economy into a single power performance metric. To calculate virtual power, an accurate measurement of the condition a runner is running in is determined. This determination may be done using sensors and GPS measurements from a phone, watch, or other device. The resulting virtual power metric is directly comparable from runner to runner. Practically, this means that the more virtual power a runner produces, either the fitter, more efficient or faster the runner is. This explains why virtual power is an important new training metric.

Virtual power provides an accurate measure of a runner's running performance that can be reliably compared from run to run, compared from runner to runner as Watts/kg, used to quantify training stress and training loads, used for accurate effort based pacing, compared over any terrain, used to estimate caloric requirements, and used to estimate a runners anaerobic and aerobic capacity.

Virtual power is calculated by accurately measuring running conditions (running condition data), including the runner's weight, incline, speed, acceleration, running surface, and apparent wind speed. The runner's weight and running surface (track, road or trail conditions) are entered by the runner prior to beginning a run, while incline, speed and acceleration data is collected using the GPS and a barometric altimeter that is built into a smart device (smart phone, smart watch, pad or any similar device). Wind is accounted for by assuming an apparent head wind equal to the runner's velocity and accounts for <5% of running power at typical running speeds. Due to the lack of available input data, the current virtual power application does not account for changes in virtual power due to wind related weather conditions. In other implementations, the device may account for changes in virtual power due to wind related weather conditions by including other sensors in the measuring device or weather data collected from remote weather stations or sites.

The running condition data is used to calculate virtual power in real-time using a formula developed by fitting published academic data on VO2 consumption under all expected running conditions. Prior to fitting, the VO2 data is converted to units of power (Watts) by accounting for metabolic efficiency.

Since a run may also include short periods of walking, the invention also parameterizes virtual power to accurately reflect performance at walking speeds. Walking is a fundamentally different and significantly more efficient form of locomotion than running. For this reason, different parameterization for virtual power at walking speeds is employed. The current approach transitions power smoothly from walking virtual power to running virtual power over a transition interval of ~0.5 mph at the typical walk/run transition speed. The typical walk/run transition speed has been shown to vary by incline and typically falls in a range of 3.5-4.5 mph.

It is noted that virtual power may not only be calculated (as described above) but may be determined by looking up an athlete's virtual power in a table or database using the calculated and processed measured conditions that are correlated and complied to equate to the virtual power of an athlete based upon those conditions. An example of the calculation of virtual power using entered and sensor based performance and environmental condition data is:

$$P = mv[a + b \exp(-\delta F_h/mg)] + F_h v \alpha$$

Where:
m=mass of the runner
v=velocity of the runner
$F_h$=the magnitude of the apparent horizontal force on the runner due to the slope of the hill, wind resistance and acceleration of the runner.
g=gravitational acceleration constant
a, b, δ, and α are constants that are determined by fitting the Power formula with available predetermined data on the running performance associated with excellent runners. These constants take on different values depending on the direction of the apparent horizontal force $F_h$ with the constraint that the virtual Power, P, and its derivative must be continuous at $F_h$=0.

In the current example, the constant α is assigned the value of "one" when running against a horizontal force (up a slope, into the wind or accelerating). However, when running with the aid of a horizontal force, the value of alpha is less than "one" since in this case it reflects the breaking power required to absorb the impact of running downhill. The value of alpha for downhill running can be determined by using the value of power output of excellent runners when running down steep slopes, since at these slopes changes in the virtual power are dominated by this term. In a similar manner, by fitting available data, appropriate values for the other constants, a, b, and 6 are determined.

In FIG. 1, a block diagram 100 of a smart device 102 in accordance with an example of an implementation of the invention is depicted. A controller 104 is coupled to a memory 106, sensors 108, GPS receiver 110, transceiver 112, display 114, and user interface 116 by communication and electrical bus 124. The controller 104 executes a plurality of instructions stored in operating system memory 118 that operates smart device 102. The instructions for a virtual power application 122 are stored in application memory 122 and executed by controller 104. In response to the instructions, the user interface 116 accepts input for the runner, display 114 displays virtual power results and notifies the runner of information that is needed. Sensors 198 may include such sensor as temperature, wind speed, altitude, etc. . . . . GPS receiver 110 receives location data and may also determine speed, direction, and altitude for the runner along with changes in speed, direction and altitude. The transceiver 112 enables the smart device to communicate 132 via WiFi/Bluetooth/cellular (i.e. 3G, 4G, GSM) with a network 126 and access such information as weather data 130 (including wind data) and/or external applications and data 128.

Figure 2:
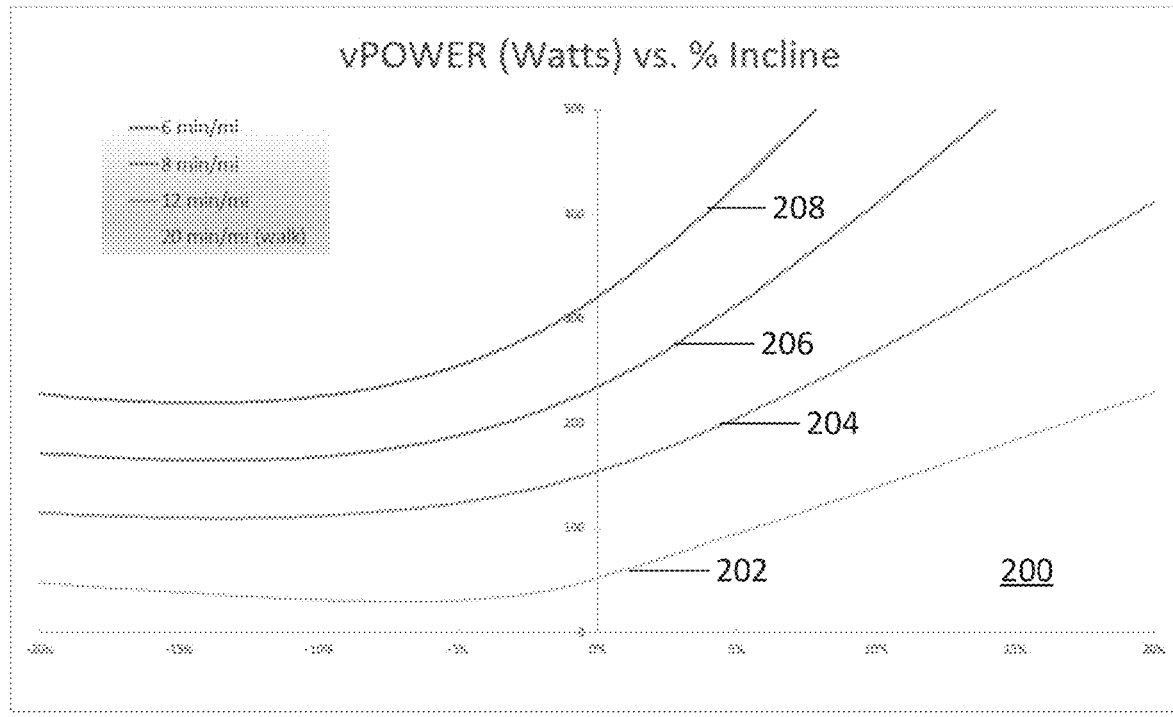
FIG. 2 illustrates a graph of virtual power vs. percent incline in accordance with an example of an implementation of the invention.

Turning to FIG. 2, an illustration 200 of a graph of virtual power vs. percent incline is depicted in accordance with an example of an implementation of the invention. It illustrates the results of virtual power calculations for different inclines for a runner at different speeds. From the graphs, it is noted the difference in walking 202 and running 204, 206 and 208.

Figure 3:
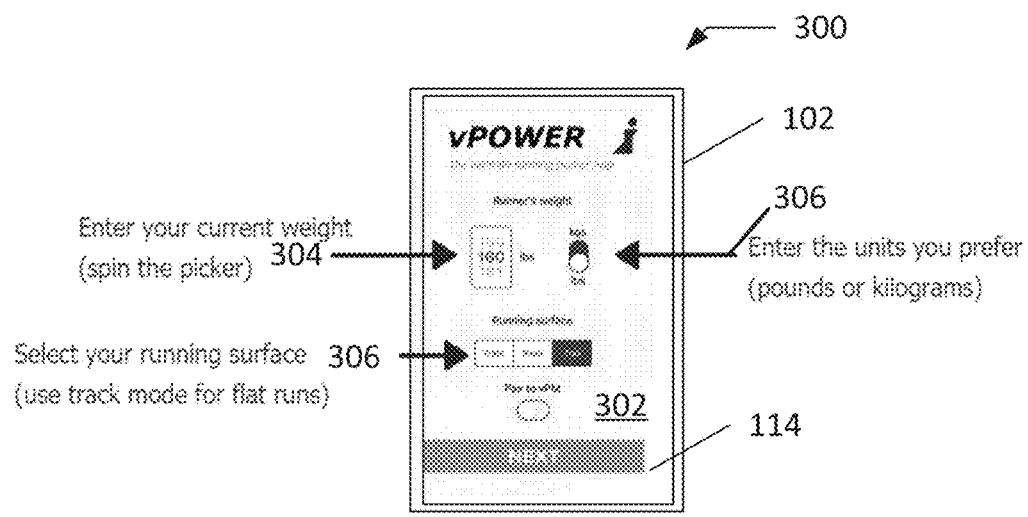
FIG. 3 is an illustration of a graphical user interface on a smart device of FIG. 1 to enter initial parameters in accordance with an example of an implementation of the invention.

In FIG. 3, an illustration 300 of a graphical user interface 302 for entering initial parameters on a display 114 of smart device 102 of FIG. 1 is depicted in accordance with an example of an implementation of the invention. A runner is able to enter their current weight 304 in pounds or kilograms and the running surface 306 (road, grass, trail, track etc.). The entered parameters are then used to calculate virtual power.

Figure 4:
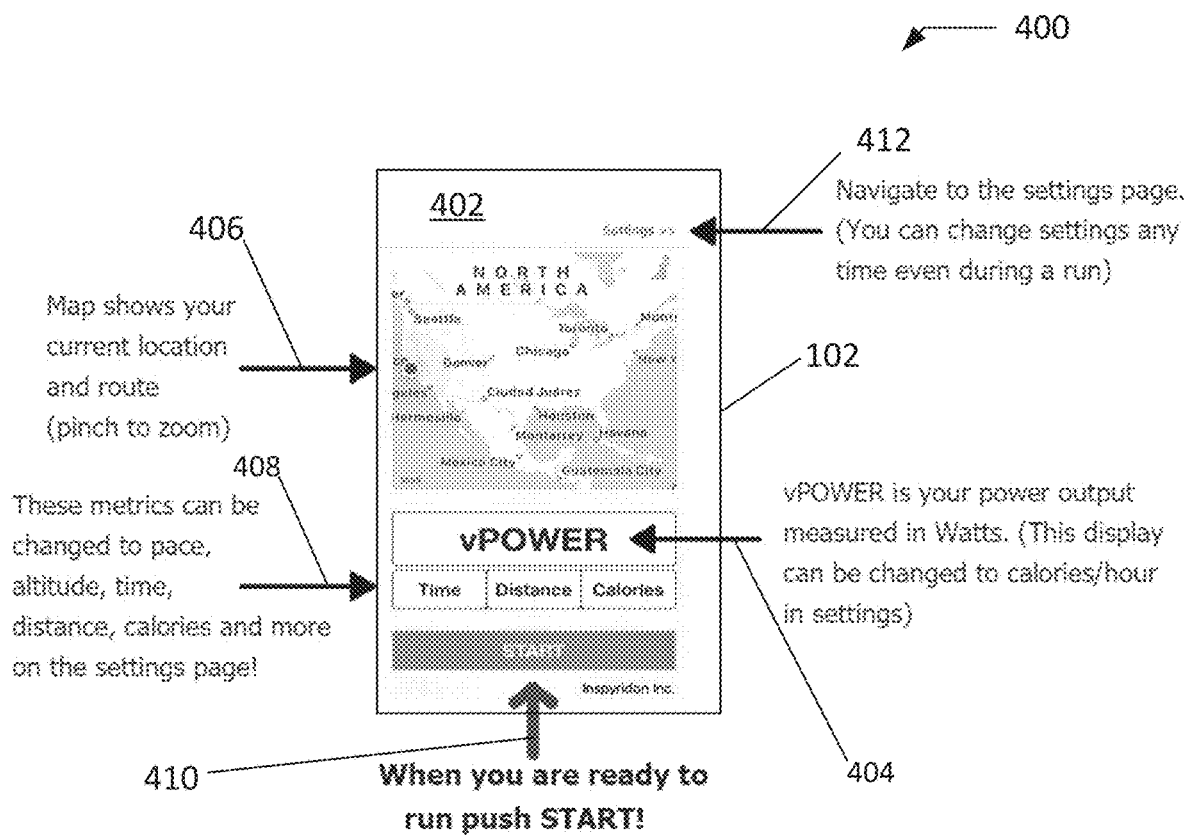
FIG. 4 is an illustration of a graphical user interface on a smart device of FIG. 1 that displays virtual power in accordance with an example of an implementation of the invention.

Turning to FIG. 4, an illustration 400 of a graphical user interface 402 on smart device 102 of FIG. 1 that displays virtual power 404 in accordance with an example of an implementation of the invention. A map 404 may be displayed along with the virtual power metric in watts 404. Additionally, pace, altitude, time, distance, calories, and other data may be selectively displayed. In the current implementation, only one metric at a time may be displayed, but in other implementations multiple metrics may be displayed. In yet other implementations, a group of metrics may be selectable and displayed at the same time. The calculation of the virtual power may be started by selecting the "START" button 410 in the graphical user interface 402.

Figure 5:
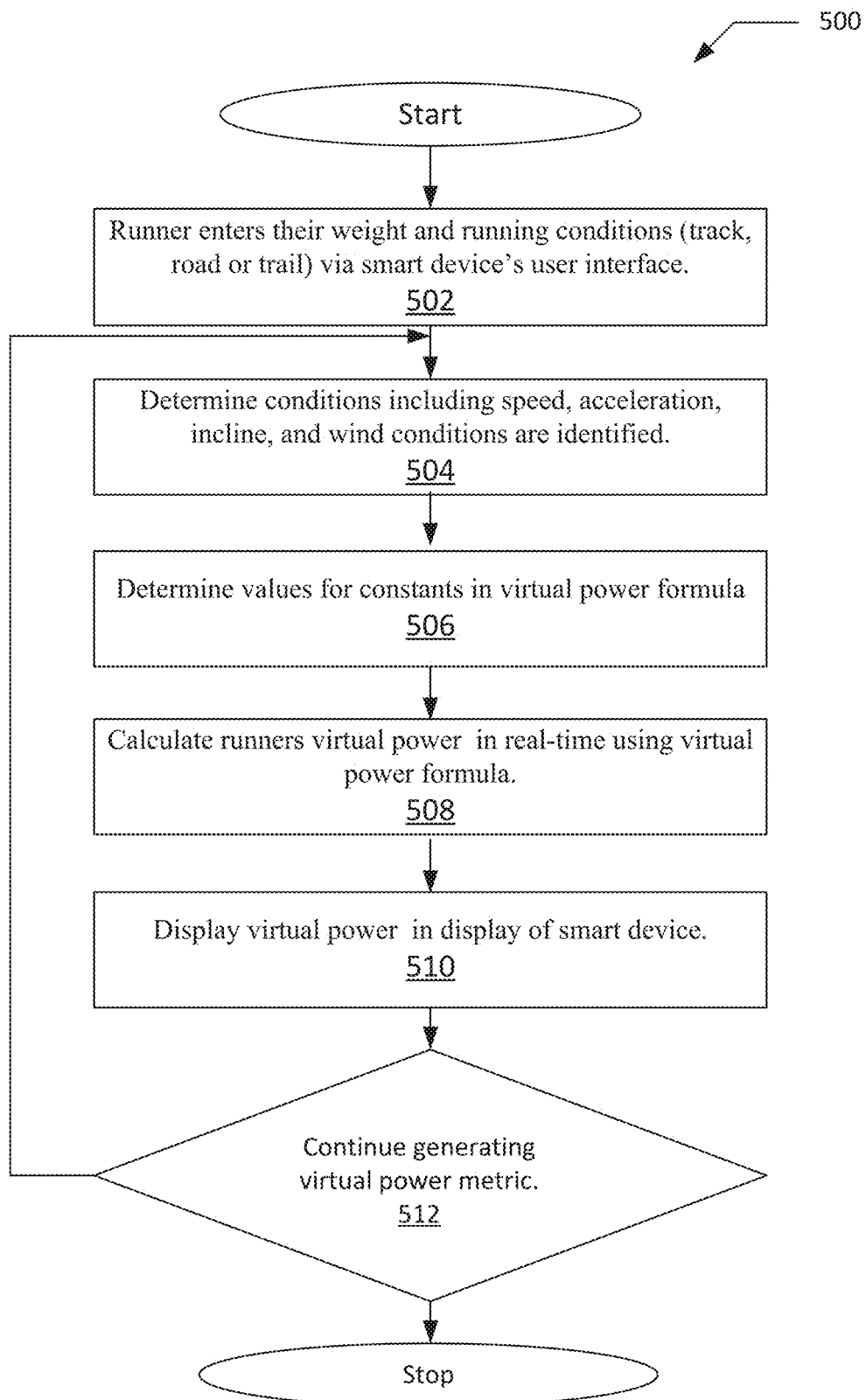
FIG. 5 is a flow diagram of the approach for determining virtual power in a smart device of FIG. 1 in accordance with an example of an implementation of the invention.

In FIG. 5, a flow diagram 500 of the approach for determining virtual power in a smart device 102 of FIG. 1 in accordance with an example of an implementation of the invention is shown. The runner enters their weight and running conditions via the smart device's user interface 302 in step 502. In step 504, the conditions of the runner's run are determined, such as speed, acceleration, incline, and wind conditions. The values for constants used in the virtual power formula are determined in step 506. The constants are then used in the virtual power formula to determine virtual power in step 508. The calculated virtual power is then displayed in the display 114 of smart device 102 in step 510. If the runner is still running, then processing continues 512 at step 504 again. Otherwise, processing of virtual power may stop in the current example.

Figure 6A:
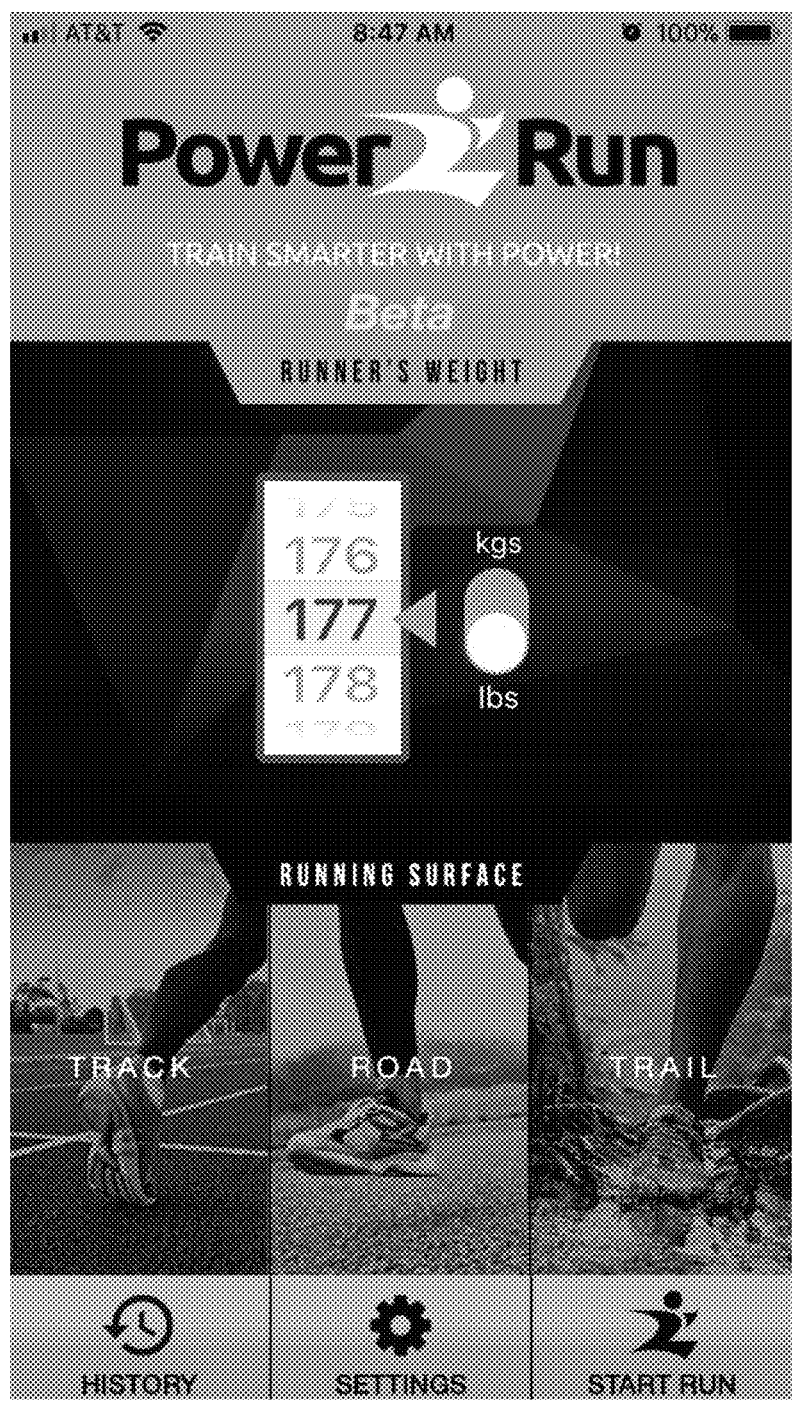
FIG. 6A is another example of an illustration of a graphical user interface on a smart device of FIG. 1 to enter initial parameters in accordance with an example of an implementation of the invention.
Figure 6B:
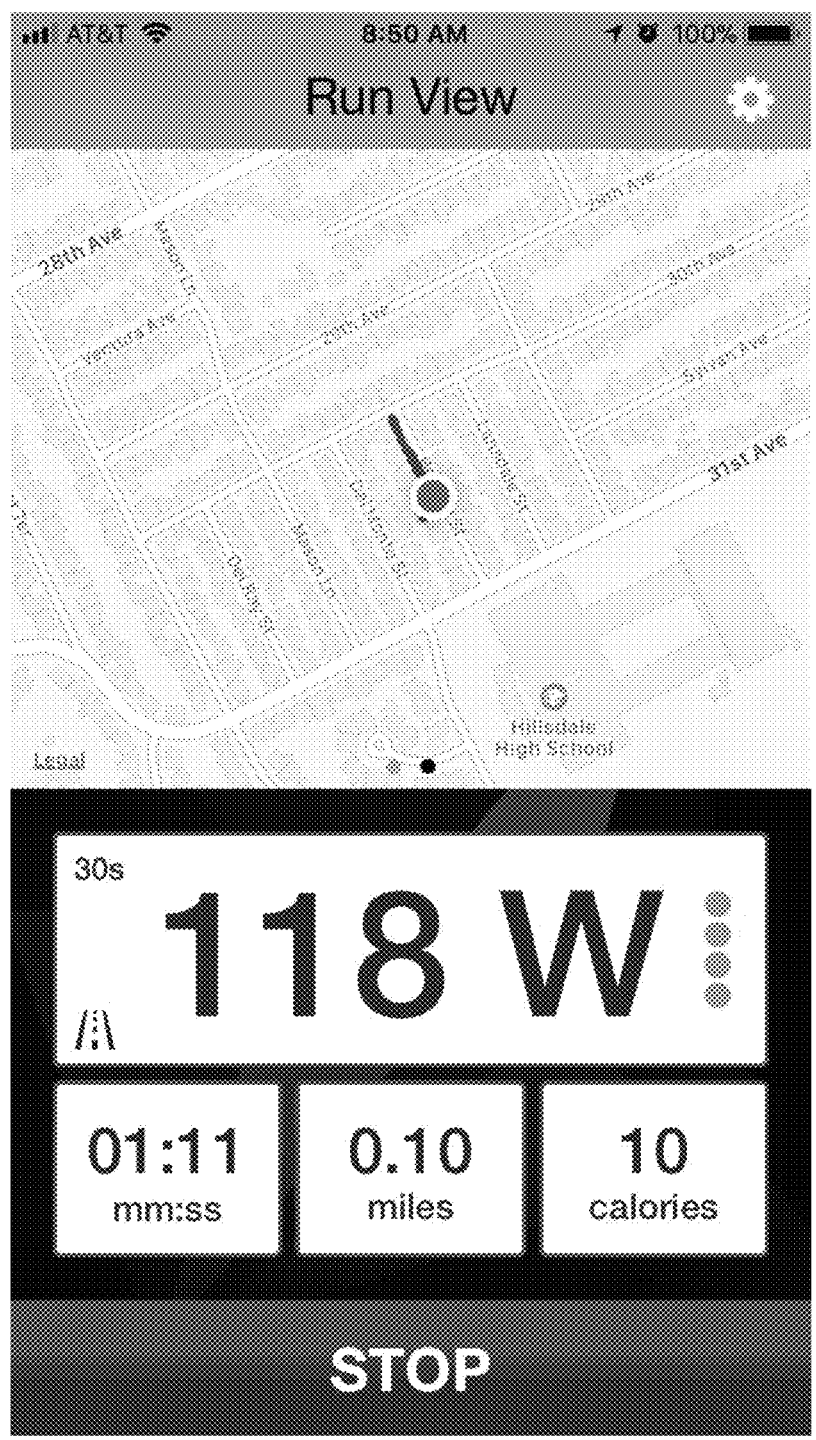
FIG. 6B is another example of an illustration of a graphical user interface on a smart device of FIG. 1 that displays virtual power in accordance with an example of an implementation of the invention.
Figure 6C:
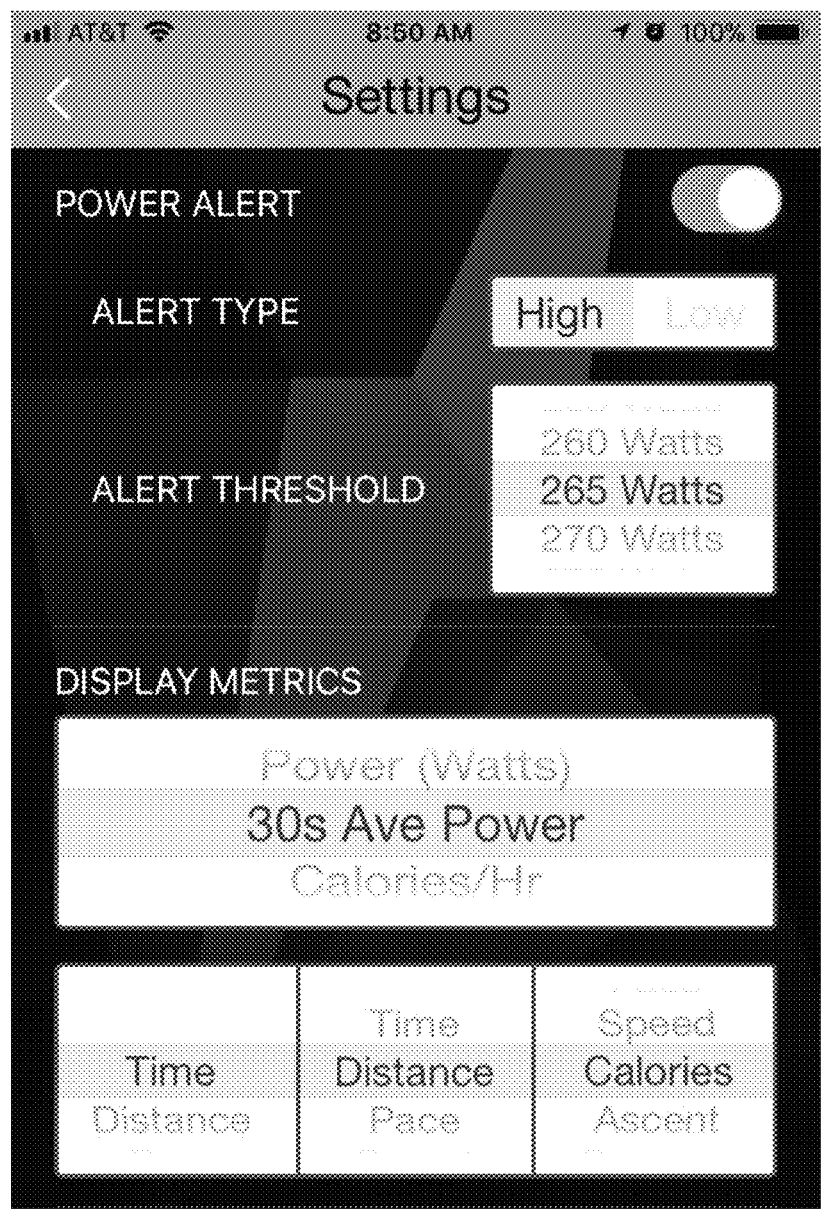
FIG. 6C is an illustration of a graphical user interface on a smart device of FIG. 1 that displays various settings in accordance with an example of an implementation of the invention.

FIGS. 6A-6C illustrates additional examples of illustrations of a graphical user interface on a smart device of FIG. 1. In particular, FIG. 6A is another example of an illustration of a graphical user interface as shown on FIG. 3 and the parameters that may be entered are the same as those shown on FIG. 3. FIG. 6B is another example of an illustration of a graphical user interface as shown on FIG. 4 that displays virtual power. FIG. 6C is an example of an illustration of the settings page on a graphical user interface on a smart device of FIG. 1. As shown in FIG. 6C, in addition to varying the display metrics, a user may also enter various alert settings to get alerted when certain virtual power thresholds are reached.

As described, the present approach uses virtual power as a runner's training metric rather than attempting to measure a runner's actual power and running economy. Since virtual power is based on running conditions alone, it directly reflects a runner's real-time performance. The virtual power metric provides a holistic view of running performance which is a better value from which to assess fitness and determine training paces. But unlike the prior VDOT approach, virtual power is a real-time metric that can be used to compare running performance under a wide variety of conditions e.g. running up and down hills, at a variety of speeds, under varying wind conditions. The present approach that calculates virtual power from running conditions is novel. It is developed by fitting published academic data on VO2 consumption under all expected running conditions to determine constants used to determine virtual power. Also, it is noted that the VO2 data is converted, prior to its use, to units of power (Watts) by accounting for metabolic efficiency used in the virtual power formula disclosed above.

It is also noted that the original motivation to create the virtual power metric was to provide runner's with a real-time training metric similar to that available to cyclists who train using power. Unlike cycling where economy of pedaling remains constant throughout a ride, direct measurements of running power has the additional problems created by changes in running economy from runner to runner and when running under different conditions. This makes it difficult to measure running power directly. However, it is not necessary to measure a runner's actual running power in order to create performance based training metric, such as virtual power. The advantage of using the virtual power metric is that it provides runners with a metric that can be:

Reliably compared from run to run
Compared from runner to runner as Watts/kg
Used to quantify training stress and training loads
Used for accurate effort based pacing
Compared over any terrain
Used to estimate caloric requirements
Used to estimate a runners anaerobic and aerobic capacity In other implementations, additional sensors may be employed to more accurately measure running conditions. Examples of such sensors may include; the use of more sensitive barometric altimeter for tracking incline changes, inertial sensing units (gyroscopes or accelerometers) to better measure the runner's real-time velocity and/or wind sensors to precisely measure the wind resistance due to changing weather conditions. Furthermore, using inertial sensors may be employed to track the run/walk transition to better account for changes in virtual power related to this transition. It is also envisioned that the same virtual power approach to calculate virtual power can be used for other endurance sports sand activities such as, but not limited to, swimming, rowing, or cycling. In yet other implementations, a virtual power approach may be adapted for use in mix activity sports, like triathletes (biking, swimming, and running).

It is understood, and is appreciated by persons skilled in the art, that one or more processes, sub-processes, or process steps in the measuring device described and approach above may be performed by hardware and/or software. In this invention, the measurements are performed by a device worn or carried by an athlete that includes hardware and software for accurately measuring running conditions and calculating virtual power. If the approach is performed by software, the software may reside in software memory (not shown) in a suitable electronic processing component or system such as, one or more of the functional components or modules described above. The software in software memory may include an ordered listing of executable instructions for implementing logical functions (that is, "logic" that may be implemented either in digital form such as digital circuitry or source code or in analog form such as analog circuitry or an analog source such an analog electrical, sound or video signal), and may selectively be embodied in any computer-readable medium for use by or in connection with an instruction execution system, apparatus, or device, such as a computer-based system, processor-containing system, or other system that may selectively fetch the instructions from the instruction execution system, apparatus, or device and execute the instructions. In the context of this disclosure, a "computer-readable medium" is any means that may contain, store or communicate the program for use by or in connection with the instruction execution system, apparatus, or device. The computer readable medium may selectively be, for example, but is not limited to, an electronic, magnetic, optical, electromagnetic, infrared, or semiconductor system, apparatus or device. More specific examples, but nonetheless a non-exhaustive list, of computer-readable media would include the following: a portable computer diskette (magnetic), a RAM (electronic), a read-only memory "ROM" (electronic), an erasable programmable read-only memory (EPROM or Flash memory) (electronic) and a portable compact disc read-only memory "CDROM" (optical). Note that the computer-readable medium may even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It will be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

I claim:

1. A device for measuring athletic performance, comprising:
   a memory storing a plurality of constants used in calculating a virtual power metric;
   a sensor or sensors for measuring an athlete's performance and determining the environmental conditions under which they are performing;
   a controller coupled to the sensor or sensors and the memory, where the controller determines a virtual power metric using the athlete's performance, environmental conditions data, and the plurality of constants stored in the memory, where the virtual power metric is calculated using laboratory data on the running economy of excellent runners under a variety of running conditions to predict the virtual power metric of the athlete based upon the determined environmental conditions; and
   a display coupled to the controller for displaying the virtual power metric.

2. The device of claim 1 where the athlete's performance data include velocity and acceleration, and are measured using a GPS receiver coupled to the controller.

3. The device of claim 2, where the environmental conditions under which the athlete is performing includes wind speed data measured by a wind speed sensor.

4. The device in claim 2, where the conditions under which the athlete is performing includes altitude gain and loss measured by an altimeter.

5. The device of claim 1, where the device is a smart device.

6. The device of claim 1, where the virtual power metric accurately predicts an athlete's virtual power in real-time.

7. A method for measuring athletic performance, comprising:
   retrieving performance and environmental condition data from a sensor or sensors using a controller;
   accessing a plurality of constants from a memory;
   calculating a virtual power metric using the performance and environmental condition data and plurality of constants from the memory, where the virtual power metric is calculated using laboratory data on the running economy of excellent runners under a variety of running conditions to predict the virtual power metric of the athlete based upon the retrieved environmental conditions; and
   displaying on a display of a device, the virtual power metric.

8. The method of claim 7 where the athlete's performance data include speed and acceleration and are measured using a GPS receiver coupled to the controller.

9. The method of claim 7 where the environmental condition data further includes, collecting environmental condition data via a user interface; and storing the environmental condition data in memory.

10. The method of claim 7, where the environmental condition data further includes, receiving wind speed data measured by a wind speed sensor.

11. The method of claim 7, where the environmental condition data further includes, receiving altitude change data from an altimeter.

12. The method of claim 7, where the device is a smart device.

13. The method of claim 7, where the virtual power metric accurately predicts an athlete's virtual power in real-time.

14. The method of claim 7, where environmental condition data includes identification of running surface.

15. A non-transitory computer readable medium having a plurality of instructions that when executed, executes the method for measuring athletic performance comprising:
   retrieving performance and environmental condition data from a sensor or sensors using a controller;
   accessing a plurality of constants from a memory;
   calculating a virtual power metric using the performance and environmental conditions data and plurality of constants from memory, where the virtual power metric is calculated using laboratory data on the running economy of excellent runners under a variety of running conditions to predict the virtual power metric of the athlete based upon the retrieved environmental conditions; and displaying on a display of a device, the virtual power metric.

16. The non-transitory computer readable medium having a plurality of instructions, that when executed, executes the method for measuring athletic performance, of claim 15 further including, collecting environmental condition data via a user interface; and storing the environmental condition data in memory.

17. The non-transitory computer readable medium having a plurality of instructions that when executed, executes the method for measuring athletic performance, of claim 15, where the athlete's performance data include speed and acceleration and are measured using a GPS receiver coupled to the controller.

18. The non-transitory computer readable medium having a plurality of instructions that when executed, executes the method for measuring athletic performance, of claim 15, where the environmental condition data further includes, receiving wind speed data from a wind speed sensor.

19. The non-transitory computer readable medium having a plurality of instructions that when executed, executes the method for measuring athletic performance, of claim 15, where the device is a smart device.

20. The non-transitory computer readable medium having a plurality of instructions that when executed, executes the method for measuring athletic performance, of claim 15, where the virtual power metric accurately predicts an athlete's virtual power in real-time.

21. The non-transitory computer readable medium having a plurality of instructions that when executed, executes the method for measuring athletic performance, of claim 15, where the environmental data includes identification of a running surface.

* * * * *